(12) United States Patent
Osman et al.

(10) Patent No.: US 6,537,441 B1
(45) Date of Patent: Mar. 25, 2003

(54) BIOSENSOR INVOLVING THE USE OF OPTICALLY SENSITIVE MOIETIES

(75) Inventors: Peter D. Osman, New South Wales (AU); Christopher J. Burns, New South Wales (AU); Alistair S. Martin, New South Wales (AU); Lionel G. King, New South Wales (AU)

(73) Assignees: Australian Membrane and Biotechnology Research, New South Wales (AU); The University of Sydney, New South Wales (AU)

( * ) Notice: Subject to any disclaimer, the term of this patent is extended or adjusted under 35 U.S.C. 154(b) by 0 days.

(21) Appl. No.: 09/446,004

(22) PCT Filed: Jun. 4, 1998

(86) PCT No.: PCT/AU98/00424
§ 371 (c)(1),
(2), (4) Date: Jul. 28, 2000

(87) PCT Pub. No.: WO98/55855
PCT Pub. Date: Dec. 10, 1998

(30) Foreign Application Priority Data

Nov. 20, 1997 (AU) .............................................. PP0449
Jun. 4, 1997 (AU) .............................................. PO7170

(51) Int. Cl.[7] .......................................... G01N 27/327

(52) U.S. Cl. .............. 205/778; 205/777.5; 204/403.01; 422/82.02; 436/524; 436/525; 436/806; 427/2.11; 427/58

(58) Field of Search ............................ 204/403, 403.01; 205/777.5, 778; 435/4, 7.5, 287.1; 427/2.11, 2.13, 58; 436/149, 518, 519, 806, 524, 525; 422/82.02

(56) References Cited

U.S. PATENT DOCUMENTS

| 4,828,960 | A |   | 5/1989 | Hertog |
|---|---|---|---|---|
| 5,234,566 | A | * | 8/1993 | Osman et al. ............... 204/403 |
| 5,798,030 | A | * | 8/1998 | Raguse et al. ............... 204/403 |
| 5,834,224 | A | * | 11/1998 | Ruger et al. ................. 204/403 |
| 5,874,316 | A | * | 2/1999 | Cornell et al. ............ 435/317.1 |
| 6,291,155 | B1 | * | 9/2001 | Raguse et al. ............... 204/400 |

FOREIGN PATENT DOCUMENTS

| AU | 80456/75 | 10/1976 |
|---|---|---|
| AU | B-54101/90 | 10/1990 |
| WO | 92/17788 | 10/1992 |
| WO | 93/10212 | 5/1993 |
| WO | 95/17483 | 6/1995 |
| WO | 97/05477 | 2/1997 |

OTHER PUBLICATIONS

Pace et al. "The gated ion channel biosensor– a functioning nano–machine", Proc. SPIE–Int. Soc. Opt. Eng., (1998), v. 3270, pp. 50–59.*
Willner et al, "Control of the Structure and Functions of Biomaterials by Light," Agnew Chem. Int. Ed. Engl., vol. 35, pp. 367–385 (1996).
Groves et al, "Micropatterning Fluid Lipid Bilayers on Solid Supports," Science, vol. 275, pp. 651–653 (1997).

* cited by examiner

Primary Examiner—Robert J. Warden, Sr.
Assistant Examiner—Kaj K. Olsen
(74) Attorney, Agent, or Firm—Nixon & Vanderhye (57) ABSTRACT

The present invention provides biosensors which include or are fabricated using optically sensitive moieties. The use of optically sensitive moieties provides advantages in the synthesis of the biosensors. Further the inclusion of optically sensitive moieties in the biosensor membrane provides an increase in the sensitivity of detection.

13 Claims, 7 Drawing Sheets

*Figure 11*

BIOSENSOR INVOLVING THE USE OF OPTICALLY SENSITIVE MOIETIES

FIELD OF THE INVENTION

The present invention relates to biosensors which include or are fabricated using optically sensitive moieties.

BACKGROUND

Biosensors have been constructed comprising biomembranes which are a double layer of closely packed amphiphilic lipid molecules. The molecules of these bilayers exhibit the random motions characteristic of the liquid phase, in which the hydrogen tails of the lipid molecules have sufficient mobility to provide a soft, flexible, viscid surface. The molecules can also diffuse sideways freely within their own monolayer so that two neighbouring lipids in the same monolayer exchange places with each other about once every microsecond, while the lipid molecules in opposite monolayers exchange places on the average of one a year.

These membranes may incorporate a class of molecules, called ionophores, which facilitate the transport of ions across these membranes Ion channels are a particular form of ionophore, which as the term implies, are channels through which ions may pass through membranes. A favoured ionophore is gramicidin A which forms aqueous channels in the membrane. Examples of such biosensors are disclosed in the following International Patent Applications, the disclosures of which are incorporated herein by cross reference:

PCT/AU88/00273, PCT/AU89/00352, PCT/AU90/00025,

PCT/AU92/00132, PCT/AU93/00509, PCT/AU93/00620,

PCT/AU94/00202, PCT/AU95/00763, PCT/AU96/00304,

PCT/AU96/00368, PCT/AU96/00369 and PCT/AU98/00482.

The first of these references discloses receptor molecules conjugated with a support that is remote from the receptor site. The support may be a lipid head group, a hydrocarbon chain, a cross-linkable molecule or a membrane protein.

The inner level of the membrane may be adjacent a solid surface with groups reactive with the solid surface, and spaced from the surface to provide a reservoir region as disclosed in U.S. Pat. No. 5,401,378.

Biosensors based on ion channels or ionophores contained within lipid membranes tethered to or deposited onto metal electrodes are disclosed in Australian Patent 623,747 and U.S. Pat. No. 5,234,566. Those references disclose a membrane bilayer in which each layer has incorporated therein ionophores and in which the conductance of the membrane is dependent upon the presence or absence of an analyte. The disclosure of Austalian Patent 623,747 (incorporated herein by reference) describes various ionophore gating mechanisms termed local disruption gating, extended disruption gating, vertical disruption gating, and extended displacement gating mechanisms to modify the conductivity of the membrane in response to the presence of an analyte. In each of those gating mechanisms an inner layer of the membrane (the layer closer to the solid electrode surface, if any) contains immobilised or tethered half membrane spanning ion channels which an outer layer contains more mobile half membrane spanning ion, channels. One method for immobilising the ion channels of the inner layer is to employ a polymerisable lipid layer and then cross-link the molecules of the inner monolayer and the ionophore. The conductivity of the membrane is altered by the extent to which opposing half membrane spanning ion channels align to establish a membrane spanning channel (dimer) for ion transmission across the membrane.

In local disruption gating receptor molecules are linked to mobile ionophores in the outer layer that are aligned with tethered or immobilised ionophores in the inner layer. The introduction of an analyte particle that binds to two adjacent receptors in the outer layer causes the disruption of the orderly alignment of the membrane spanning ionophore. In the case of local disruption gating a loss of conductivity occurs due to the deformation of the ionophores of the outer layer caused by the bonding of the analyte with the adjacent receptors.

The mechanism of extended disruption gating is similar, except that the displacement of the mobile ionophore is greater. In extended disruption gating the binding of pairs of receptors to the same analyte particle cause the outer layer ionophores to move completely out of alignment with the inner layer ionophores.

The mechanism of vertical disruption gating is also similar. In that case the presence of the analyte particle bound to two receptor molecules causes a separation of the two layers that disrupts the continuity of the ion channel across the membrane.

The mechanism of extended displacement gating utilises two different receptors that bind to each other and are linked receptively to a half membrane ionophore and a membrane molecule. The binding of these two receptor molecules to each other displaces the ionophore and disrupts conductivity. The analyte competes with the second receptor for the binding site on the first receptor. The presence of the analyte breaks the bond between the two receptors and allows the half membrane ionophores to realign (dimerize) and provide an ion conductive path. Each of these mechanisms has in common that the binding of the analyte to the receptor molecule causes a change in the relationship between two half membrane spanning monomers such that the flow of ions across the membrane via the ionophores is allowed or prevented.

In a number of sensing applications it is beneficial to incorporate within the one detection cell a positive or negative control to add to the utility of the biosensor. As will be recognised the fabrication of a biosensor having discrete areas of membrane which act as either a test area or control area can be very complex. The present inventors have developed methods by which such biosensors may be fabricated in a less complex manner using optically sensitive moieties.

In a number of sensing applications it is beneficial to incorporate within the one detection cell a positive or negative control to add to the utility of the biosensor. As will be recognised the fabrication of a biosensor having discrete areas of membrane which act as either a test area or control area can be very complex. The present inventors have developed methods by which such biosensors may be fabricated in a less complex manner using optically sensitive moieties.

SUMMARY

Accordingly in a first aspect the present invention consists in a method of fabricating a biosensor in which there is at least one discrete test and at least one discrete control zone, the method comprising the following steps:

(i) providing a conductive substrate;
(ii) forming a membrane including membrane spanning lipids and ion channels comprising first and second half membrane spanning monomers such that the membrane is tethered to the conductive substrate such that a functioning reservoir exists between the membrane and the conductive substrate;
(iii) linking a ligand reactive with an analyte of interest to the ion channel and linking a ligand reactive with an analyte of interest to the membrane spanning lipid components of the tethered membrane via photocleavable linkers; and
(iv) exposing the membrane to a focused light source to cleave the photocleavable linkers thereby releasing the ligands from the ion channel and membrane spanning lipid components in discrete areas of the membrane.

In a preferred embodiment the method further includes the following step:
(v) binding control ligands to the ion channels and membrane spanning lipid components after the ligands have been removed in step (iv).

In a further preferred embodiment the membrane is rinsed between steps (iv) and (v).

In a second aspect the present invention consists in a method of fabricating a biosensor in which there is at least one discrete test and at least one discrete control zone, the method comprising the following steps:
(i) providing a conductive substrate;
(ii) forming a membrane including membrane spanning lipids and ion channels comprising first and second half membrane spanning monomers such that the membrane is tethered to the conductive substrate such that a functioning reservoir exists between the membrane and the conductive substrate;
(iii) providing on the ion channels and membrane spanning lipids a photoactivatable group which when illuminated will bind a receptor;
(iv) illuminating discrete areas of the membrane and linking a ligand reactive with an analyte of interest to the ion channel and membrane spanning lipid components of the tethered membrane via photoactivatable group to form test areas;
(v) removing unbound ligand; and
(vi) linking a control ligand to the remainder of the ion channels and membrane spanning lipid components of the tethered membrane to form control areas.

The photocleavable linkers may be any of a number of such molecules known in the art (eg see Pillai (1980)). The photoactivatable groups may be any number of such groups known in the art, such as, for example, photoactivatable biotins described by Pirrung (1996) or Cass (1996).

The conductive substrate may, of course, be any of a range of such substrates known in the art, for example gold coated glass or silicon.

One advantage of this approach is the ability to fabricate differential electrodes (active versus control) with the high degree of spatial resolution achievable using optical methods, and unachievable using other methods (such as controlled liquid deposition). This high degree of spatial resolution would result in improved common mode rejection and therefore improved sensitivity as well as simplifying the manufacturing process.

In a third aspect the present invention consists in an improved biosensor, the biosensor comprising a membrane and an electrode having a conductive substrate, the membrane including membrane spanning lipids and ion channels comprising first and second half membrane spanning monomers, the membrane being attached to the conductive substrate such that a functioning reservoir exists between the membrane and the conductive substrate, ligands specific for an analyte attached the ion channels and membrane spanning lipids, the improvement comprising providing on at least one of the first and second half membrane spanning monomers a photocleavable/switchable group which inhibits dimer formation.

In a fourth aspect the present invention consists in an improved biosensor, the biosensor comprising a membrane the conductance/impedance of which is altered by the presence or absence of an analyte and a conductive substrate, the membrane including membrane spanning lipids and ion channels comprising first and second half membrane spanning monomers such that the membrane is tethered to the conductive substrate such that a functioning reservoir exists between the membrane and the conductive substrate, and ligands attached to the ion channels and membrane spanning lipids, the improvement comprising providing on at least one of the first and second half membrane spanning monomers or membrane spanning lipids a photoswitchable group derived from a compound in accordance with Formula 1.

Formula 1 wherein $R_1$ represents 0 to about 3 groups where each is independently H or saturated or unsaturated, substituted or unsubstituted $C_{1-10}$ hydrocarbon, preferably saturated or unsaturated, substituted or unsubstituted $C_{1-4}$ hydrocarbon; $R_2$ represents 0 to about 3 groups where each is independently hydrogen or saturated or unsaturated, substituted or unsubstituted $C_{1-10}$ hydrocarbon, preferably saturated or unsaturated, substituted or unsubstituted $C_{1-4}$ hydrocarbon; Y represents H, saturated or unsaturated, substituted or unsubstituted $C_{1-10}$ hydrocarbon, preferably saturated or unsaturated, substituted or unsubstituted $C_{1-4}$ hydrocarbon, $COR_6$, $CONR_7R_8$, $COOR_{14}$, $S(O)_nR_{15}$ where n is 0, 1 or 2, $R_6$, $R_7$, $R_8$, $R_{14}$ and $R_{15}$ are each independently represent H, saturated or unsaturated, substituted or unsubstituted $C_{1-10}$ hydrocarbon, preferably saturated or unsaturated, substituted or unsubstituted $C_{1-4}$ hydrocarbon or aryl; $R_9$ is —C(O)X where X represents H, saturated or unsaturated, substituted or unsubstituted $C_{1-10}$ hydrocarbon, preferably saturated or unsaturated, substituted or unsubstituted $C_{1-4}$ hydrocarbon, or OH, or $OR_{10}$ in which $R_{10}$ is alkyl, or $NR_{11}R_{12}$ in which $R_{11}$ and $R_{12}$ are H, alkyl or taken together with N form a ring, or aryl or $R_9$ together with $R_1$ form a substituted or unsubstituted 5–6 member cyclic or heterocyclic ring; Z represents O or $NR_{15} R_{13}$ is H, saturated or saturated, substituted or unsubstituted $C_{1-10}$ hydrocarbon, preferably saturated or unsaturated, substituted or unsubstituted $C_{1-4}$ hydrocarbon or aryl.

The compound will include a functional group at Y or $R_9$ such that the compound can be linked to at least one of the first and second half membrane spanning monomers or membrane spanning lipids.

Particularly preferred compounds from which the photoswitchable linkers are derived are shown in Formula 2 below.

Formula 2 wherein $R_1$ represents 0 to about 3 groups where each is independently hydrogen or saturated or unsaturated, substituted or unsubstituted $C_{1-10}$ hydrocarbon, preferably saturated or unsaturated, substituted or unsubstituted $C_{1-4}$ hydrocarbon; $R_2$ represents 0 to about 3 groups where each is independently hydrogen or saturated or unsaturated, substituted or unsubstituted $C_{1-10}$ hydrocarbon, preferably saturated or unsaturated, substituted or unsubstituted $C_{1-4}$ hydrocarbon; X represents H, saturated or unsaturated, substituted or unsubstituted $C_{1-10}$ hydrocarbon, preferably saturated or unsaturated, substituted or unsubstituted $C_{1-4}$ hydrocarbon, or aryl, or OH, or $OR_{10}$ in which $R_{10}$ is alkyl, or $NR_{11}R_{12}$ in which $R_{11}$ and $R_{12}$ are H, alkyl or taken together with N form a ring,; Y represents H, or saturated or unsaturated, substituted or unsubstituted $C_{1-10}$ hydrocarbon, preferably saturated or unsaturated, substituted or unsubstituted $C_{1-4}$ hydrocarbon, $COR_6$, $CONR_7R_8$, $COOR_{14}$, $S(O)_nR_{15}$ where n is 0, 1 or 2, $R_6$, $R_7$, $R_8$, $R_{14}$ and $R_{15}$ are each independently represent H, saturated or unsaturated, substituted or unsubstituted $C_{1-10}$ hydrocarbon, preferably saturated or unsaturated, substituted or unsubstituted $C_{1-4}$ hydrocarbon or aryl; Z represents O or $NR_{15}R_{13}$ is H, saturated or unsaturated, substituted or unsubstituted $C_{1-10}$ hydrocarbon, preferably saturated or unsaturated, substituted or unsubstituted $C_{1-4}$ hydrocarbon or aryl.

Figure 10:
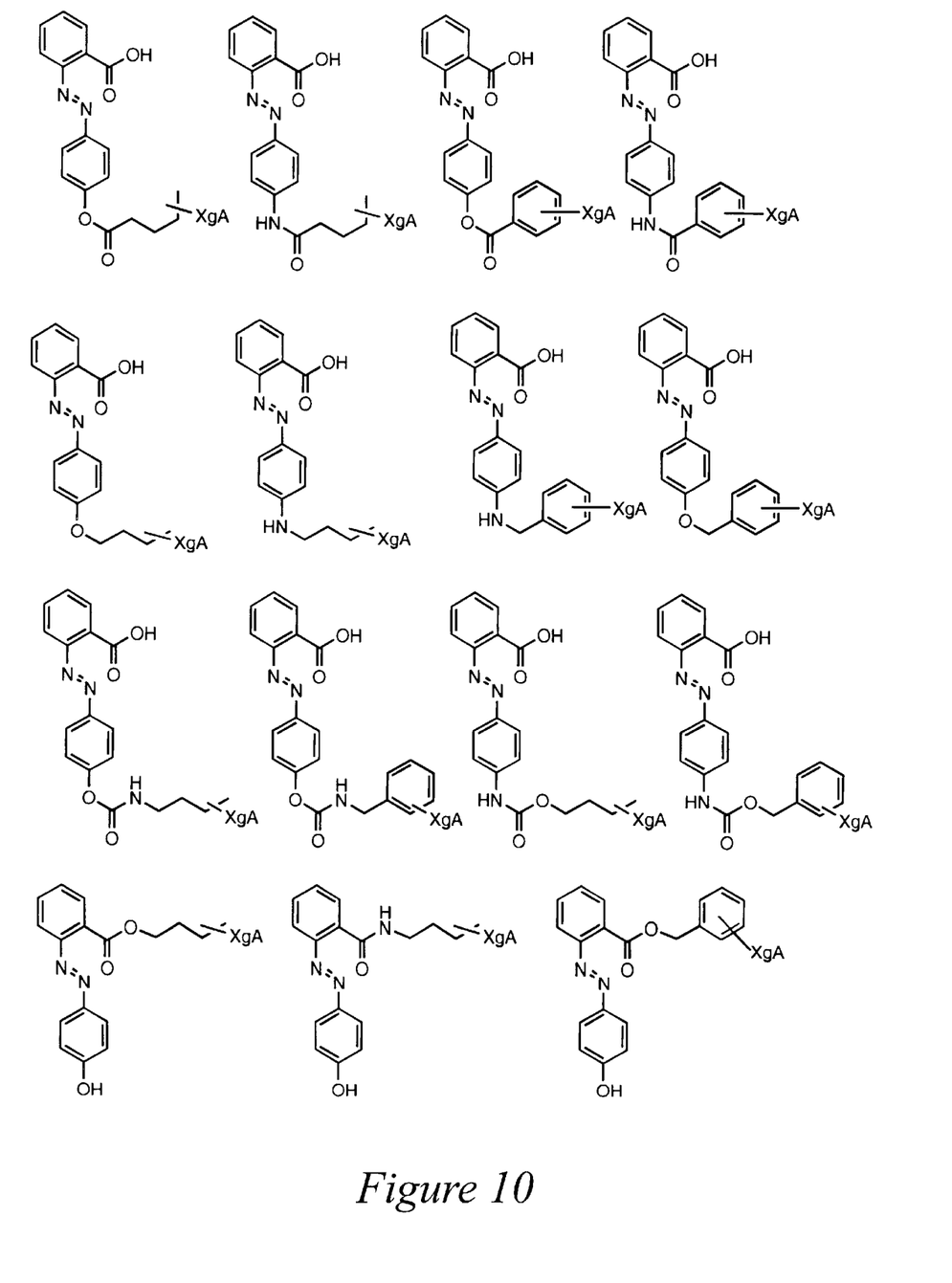
FIG. 10 shows the structure of some of the compounds of the present invention. X is a water soluble linker to gramicidin, such as a polyethylene glycol or an aminocaproyl oligomer, gA is gramicidin.

Specific examples of suitable photoswitchable linkers that are suitable for use in the present invention are shown in FIG. 10.

It will be appreciated that certain compounds of Formula 1 are novel and the present invention therefore provides, in a fifth aspect, compounds in accordance with Formula 1, provided that when $R_9$ is —C(O)X and X is H, at least one of $R_1$, $R_2$, or $R_3$ or Y is other than H.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

BRIEF DESCRIPTION OF THE FIGURES

In order that the nature of the present invention may be more clearly understood preferred forms thereof will now be described with reference to the following non-limiting examples and Figures in which.

ABBREVIATIONS

| | |
|---|---|
| gA | gramicidin A |
| SA | streptavidin |
| MSL | Membrane Spanning Lipid |
| HABA | hydroxyazobenzene-benzoic acid |

Figure 1:
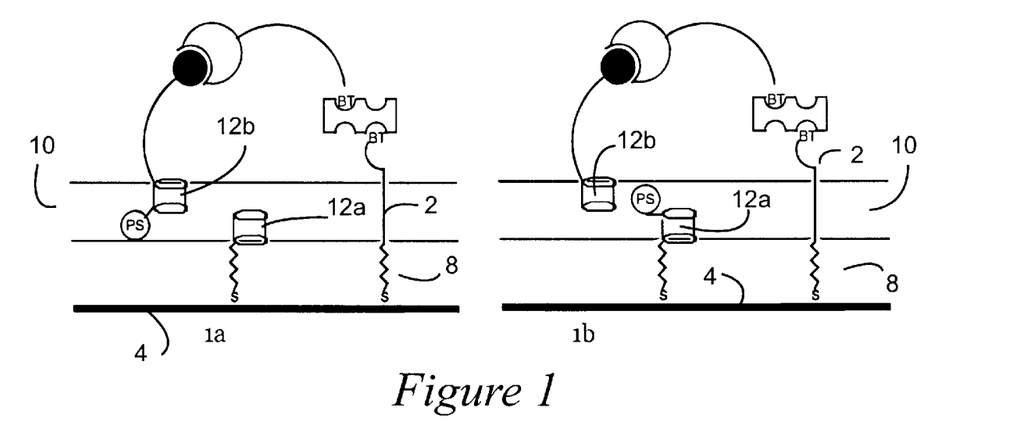
FIGS. 1a and 1b are a schematic drawings of embodiments of the invention.

Examples of an improved biosensor in accordance with the invention is shown schematically in FIGS. 1a and 1b. Membrane 10 is formed by membrane spanning lipids 2 tethered to conductive surface 4 such that there is a functioning reservoir 8 between the membrane 10 and the conductive surface 4. The membrane 10 also comprises first and second half membrane spanning monomers 12a, 12b, one of the monomers 12a being tethered to the conductive surface 4. A photoactivatable/photoswitchable group PS is provided on monomer 12a (FIG. 1a) or monomer 12b (FIG. 1b) the group PS preventing dimer formation between by the first and second monomers 12a, 12b.

The improved biosensor can be advantageously used in the detection of an analyte. An exemplary protocol for use of this type of biosensor is as follows.

An initial measurement of biosensor impedance is made and the sample suspected to contain the analyte is then added. A second measurement is made and a light source is triggered on. A third measurement of the time course response to light is made. The light source is then triggered off and a fourth measurement of the time course response to the removal of light is made. These later steps may be repeated, switching the light on and off.

Various combinations and subsets of the later measurement steps can be used depending on the type of photogroup and the level of sensitivity required. Such a construct would not allow a real gating response until illumination, and would therefore allow for non-specific effects (e.g. caused by serum addition) to be separately determined, and removed from the real gating response.

Figure 2:
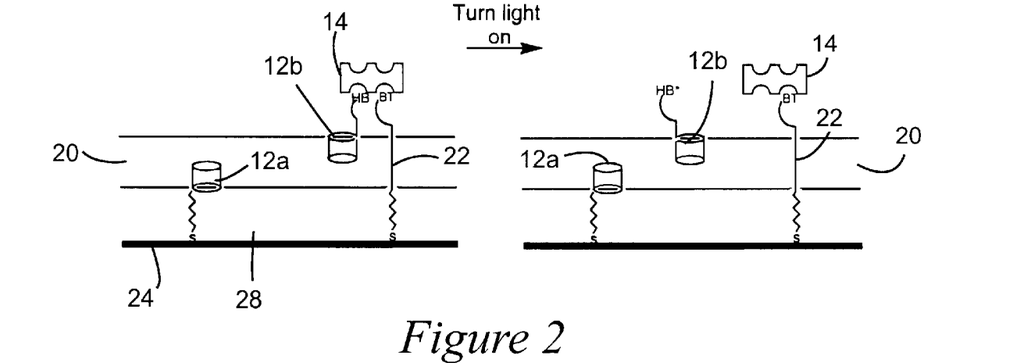
FIG. 2 is a schematic drawing of a further embodiment of the invention, where BT is biotin, HB is a photoswitchable group which binds to streptavidin in one resting form (HB) and not in its photoactive form (HB*)

The benefits of another fabrication protocol is shown schematically in FIG. 2. Membrane 20 is formed from membrane spanning lipids 22 and ion channels comprising first and second half membrane spanning monomers 12a, 12b, the membrane being attached to the conductive substrate 24 such that a functioning reservoir 8 exists between the membrane and the conductive substrate. The half membrane spanning monomer 12b remote from the conductive substrate is associated with streptavidin 14 through photo-switchable binder in its resting form HB whilst membrane spanning lipids 22 are associated with streptavidin 14 via biotin BT. When the membrane is exposed to light, the photoswitchable binder is converted to its non-photoactive form HB* releasing the streptavidin in the process. This procedure may be used to minimise any monomer-streptavidin-membrane spanning lipid linkages.

Accordingly, in a fifth aspect the present invention consists in a method comprising the following steps:
 (i) providing a conductive substrate;
 (ii) forming a membrane including membrane spanning lipids and ion channels comprising first and second half membrane spanning monomers, the membrane being attached to the conductive substrate such that a functioning reservoir exists between the membrane and the conductive substrate;
 (iii) providing on the half membrane spanning monomer remote from the conductive substrate a photoswitchable binder to streptavidin and providing biotin on the membrane spanning lipid;
 (iv) adding streptavidin;
 (v) triggering a light source and rinsing;
 (vi) triggering the light source off and adding streptavidin;
 (vii) optionally repeating steps (v) and (vi); and
 (viii) adding ligands specific to an analyte to the ion channels and membrane spanning lipids.

It is preferred that the photoswitchable binder to streptavidin is caged biotin, HABA or derivative thereof. Preferably the photoswitchle binder is caged biotin or a compound in accordance with Formula 1 above.

As mentioned above, the aim here is to minimise the formation of any gA-SA-MSZ linkages (i.e streptavidin gating). The advantage of this process is that streptavidin gating is reduced and thus the dynamic range is improved. Note an alternative version is that in step (v) the rinsing step can be avoided, meaning that additional SA in step (vi) need not be added.

Figure 3:
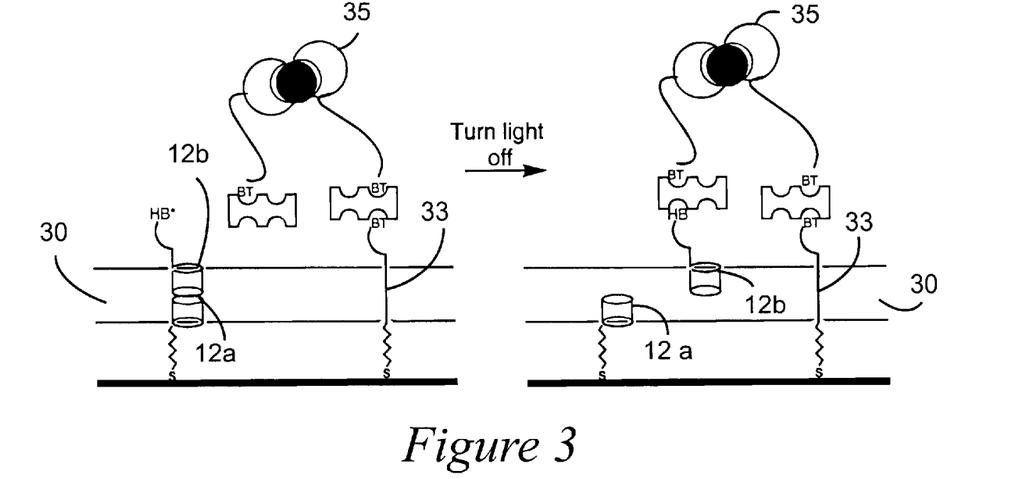
FIG. 3 is a schematic drawing of a further embodiment of the invention, where BT is biotin, HB is a photoswitchable group which binds to streptavidin in one resting form (HB) and not in its photoactive form (HB*)

A method for using photoswitchable linkers during measurement of analyte responses to improve sensitivity by separating any non-specific effect (caused during analyte addition) from the gating response (see FIG. 3).

As shown in FIG. 3, a tethered membrane assembly 30 is made with biotinylated MSL 33 and gA 12b bearing a photoswitchable group HB derived from a compound in accordance with Formula 1. A biotinylated antibody streptavidin complex 35 is then introduced into the electrolyte solution. The light source is then switched on so that the antibody complex links to the biotinylated MSL but not to the photoswitchable group gA. The analyte is then added and continually stirred and allowed to incubate so that analyte links to MSL via antibody streptavidin biotin complex. (Note at this point there is no crosslinking of MSL to gA or gA to gA because light is on). The solution is then rinsed so that unlinked antibody is removed. An impedance measurement is then made which gives the channel on baseline. Impedance measurements continue and then the light is switched off. The time course of gating is measured as gramicidin crosslinks to MSL via a photoswitchable group-streptavidin-biotin-antibody-analyte-antibody-biotin-streptavidin-photoswitchable group-MSL complex.

The advantages are improved dynamic range due to reduction of streptavidin gating and also an increase in sensitivity as the long incubation time required to crosslink the antibody to MSL no longer limits the rate of change of gating which is carried out rapidly after the crosslinking has occurred (this assumes that off times are significantly longer than on times). Further, analyte addition artifacts are avoided and thorough mixing can be carried out, and also this method is suitable for optically phase locked loop approaches.

Figure 4:
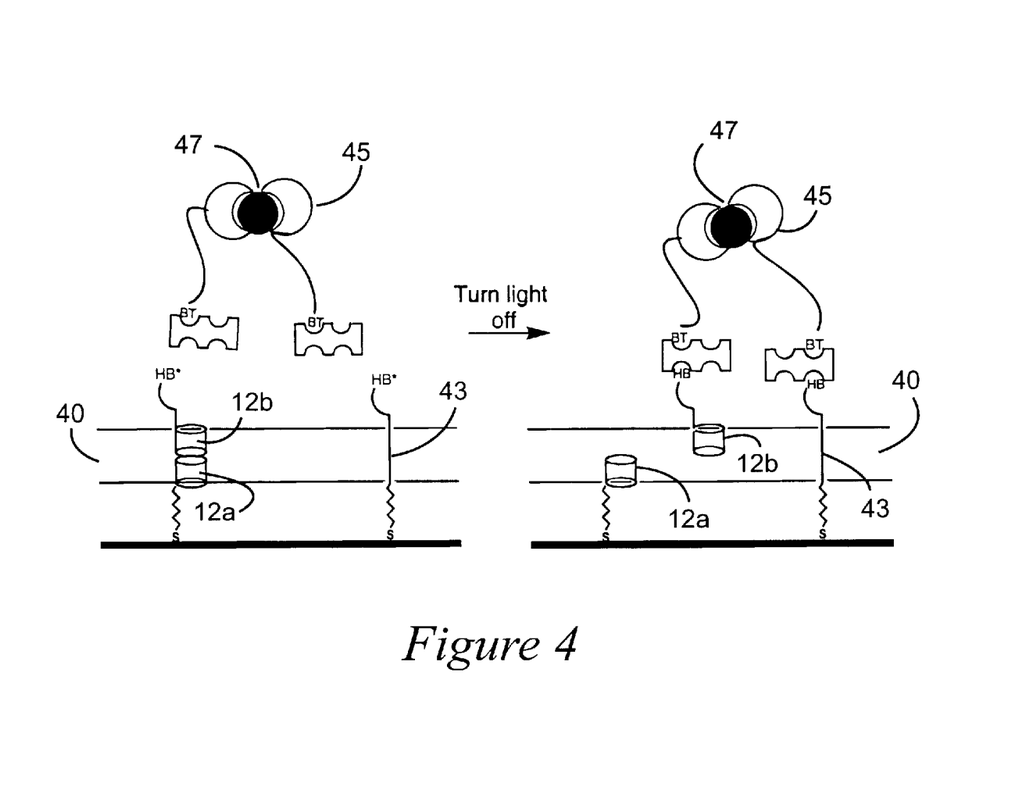
FIG. 4 is a schematic drawing of a further embodiment of the invention, where BT is biotin, HB is a photoswitchable group which binds to streptavidin in one resting form (HB) and not in its photoactive form (HB*)

A method for using photoswitchable linkers during measurement of analyte responses to improve sensitivity is shown in FIG. 4.

Referring to FIG. 4, a tethered membrane assembly 40 is made with MSL 43 and gA 12b both bearing a photoswitchable group HB in accordance with the invention. A biotinylated antibody streptavidin complex 45 is then introduced into the electrolyte solution. The light source is switched on so that the antibody complex is not bound to either MSL or gA. Analyte is added and continually stirred and allowed to incubate so that analyte 47 crosslinks all antibody-streptavidin complexes. Impedance measurements then commence which gives the channel on baseline.

Impedance measurements continue and then the light is switched off whilst impedance measurements are made for a further period of time. The time course of gating is measured as gramicidin crosslinks to MSL via a photoswitchable group-streptavidin-biotin-antibody-analyte-antibody-biotin-streptavidin-biotin-MSL complex.

There are four principal advantages to this method; 1. An amplification in sensitivity is possible where the on rate of the optically switchable group is significantly greater than the on-rate of the antibody to the analyte, and the off times are greater than both, 2. The analyte binding is carried out in three dimensions rather than two, 3. Analyte addition artifacts are avoided and thorough mixing can be carried out, and 4. This method is suitable for optically phase locked loop approaches.

Figures 5, 6:
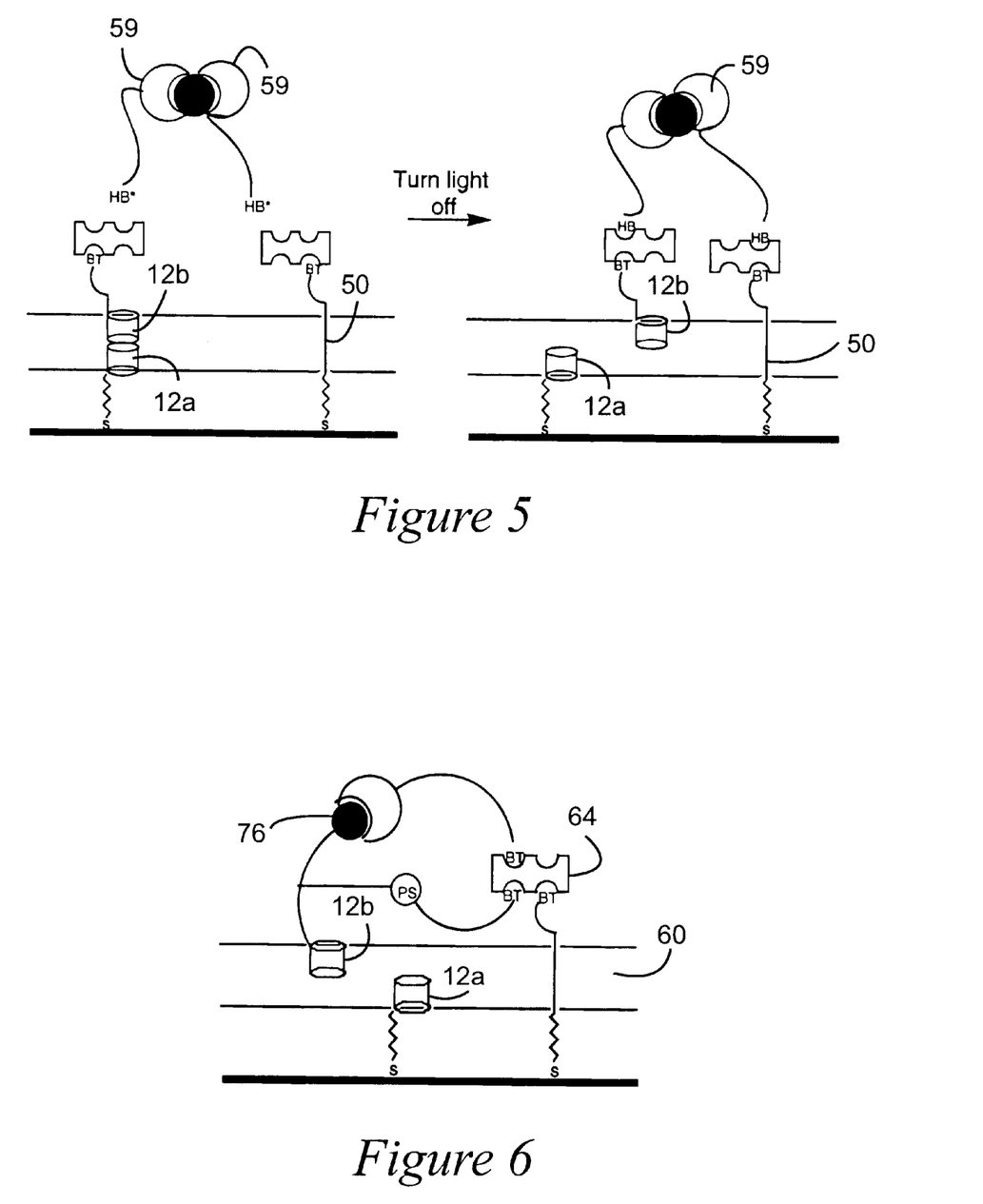
FIG. 5 is a schematic drawing of a further embodiment of the invention, where BT is biotin, HB is a photoswitchable group which binds to streptavidin in one resting form (HB) and not in its photoactive form (HB*)
FIG. 6 is a schematic drawing of a further embodiment of the invention, where BT is biotin, PS is a photoswitchable group.

A method for using photoswitchable linkers during measurement of analyte responses to improve sensitivity is shown in FIG. 5.

These methods can be modified by using antibodies 59 bearing a photoswitchable group HB instead of the gA 12 or MSL 50. In this case the advantages are analyte addition artifacts are avoided and thorough mixing can be carried out, and this method is suitable for optically phase locked loop approaches.

A method for using photoswitchable linkers during measurement of analyte responses to improve sensitivity in a competition assay (such as depicted in FIG. 6) wherein non-specific effects are separated from the real gating response.

A tethered bilayer 60 employing a gramicidin (or other ion channel) derivative 12 which bears a derivative of the required analyte 67 and a photoswitchable group PS which binds to streptavidin 64 is produced. A measurement of biosensor impedance is made then the analyte is added. A second measurement is made then a light source is triggered on. A third measurement of the time course response to light is made then the light source is triggered off. A fourth measurement of the time course response to the removal of light is then made.

The photoswitchable group could of course replace biotin. Such a group may be photoswitchable group or a derivative thereof.

Figure 7:
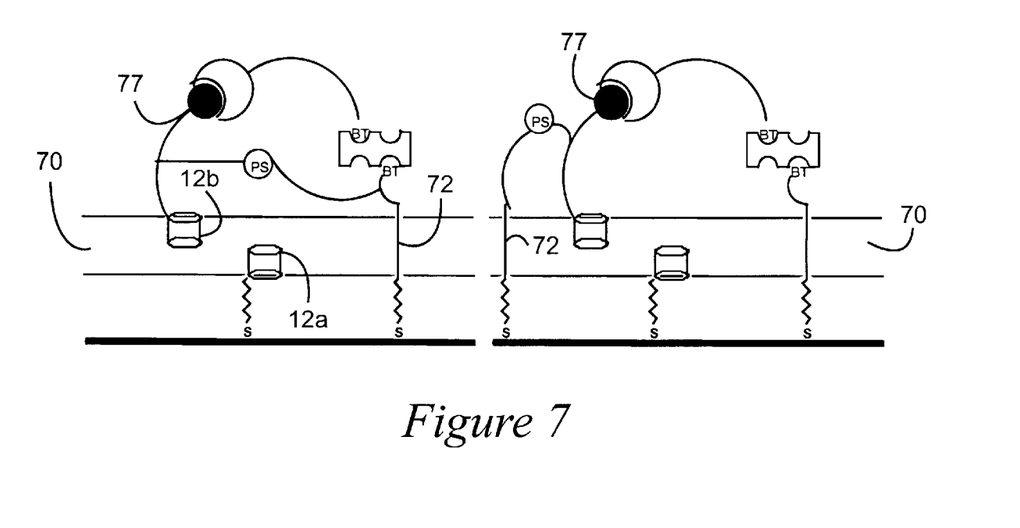
FIG. 7 is a schematic drawing of a further embodiment of the invention, where BT is biotin, PS is a photoswitchable group.

A method for using photoswitchable linkers during measurement of analyte responses to improve sensitivity ill a competition assay (such as depicted in FIGS. 7a and 7b) wherein any non-specific effects (caused during analyte addition) can be separated from the gating response.

A tethered bilayer 70 employing a gramicidin (or other ion channel) derivative 12 which bears a derivative of the required analyte 77 and a photoswitchable group PS connected to a membrane spanning lipid 72 is produced. A measurement of biosensor impedance is then made prior to addition of analyte. Analyte is added and a second measurement is made. A light source is then triggered on and a third measurement of the time course response to light is made. The light source is then triggered off and a fourth measurement of the time course response to the removal is made.

Figure 8:
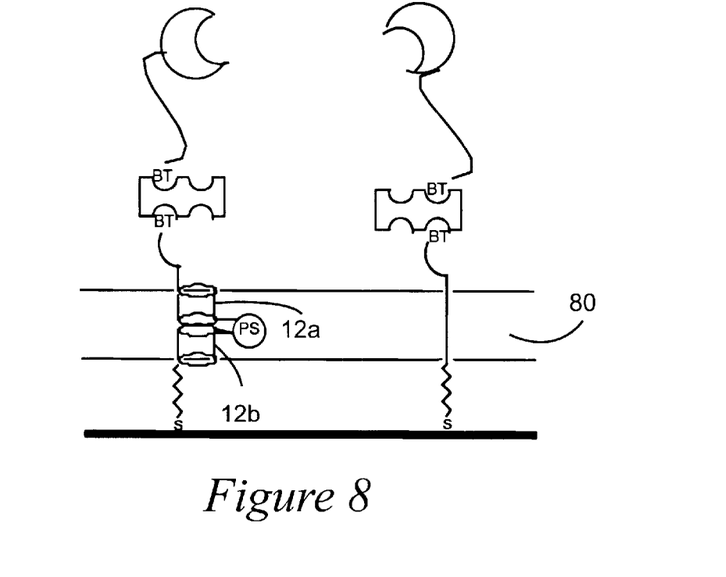
FIG. 8 is a schematic drawing of a further embodiment of the invention, where BT is biotin, PS is a photoswitchable group

A method for using photoswitchable linkers during measurement of analyte responses to improve sensitivity in a lateral segregation assay wherein any non-specific effects (caused during analyte addition) can be separated from the gating response (such as depicted in FIG. 8).

Figure 9:
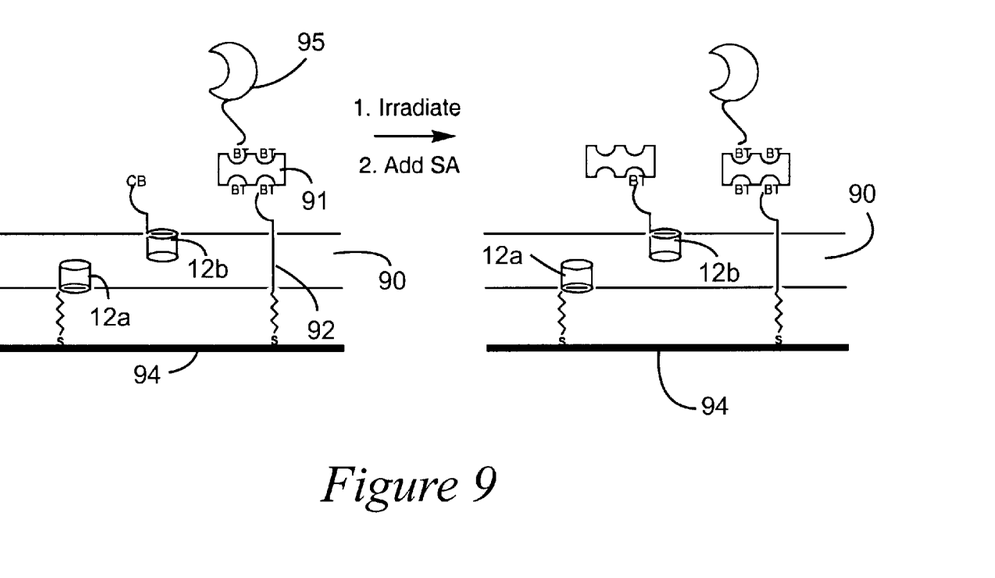
FIG. 9 is a schematic drawing of a further embodiment of the invention, where BT is biotin, CB is a caged biotin.

A tethered bilayer 80 employing a gramicidin (or other ion channel) derivative 12b which bears a derivative of the required analyte and a photoswitchable PS tether to the bottom layer gramicidin 12a (or other ion channel) is produced. A measurement of biosensor impedance is made and the analyte is added. A second measurement is then made and a light source is triggered on. A third measurement of the time course response to light is made then the light source is triggered off. A fourth measurement of the time course response to the removal is then made.

ii) manufacture a tethered bilayer 90 employing a gramicidin (or other ion channel) 12b derivative which bears a caged biotin CB iii) streptavidin 91 is added to the system, and attaches to biotin on the MSL4XB 92 iv) a biotinylated receptor 95 is added to the system, and attaches to the SA on MSL4XB v) further biotin is added to block the remaining binding sites on SA vi) a light source is triggered on vii) streptavidin is added to the system and attaches to newly generated biotin (on the gramicidin)

viii) a biotinylated receptor is added to the system, and attaches to the SA on gramicidin ix) analyte is added to the system x) an impedance measurement is made

The advantage of this manufacture process is that formation of gA-SA-MSL linkages (i.e. streptavidin gating) is minimised and thus the dynamic range is improved. A further advantage is that receptors can be selected to bind specifically at MSL4XB and the gramicidin derivative, which in turn may improve the response.

Materials and Methods

The photoswitchable ligands of the general formulae 1 and 2 are prepared by well known synthetic procedures. For example, the coupling of diazo aromatics with substituted phenols and their derivatives, has been well documented (Berwick 1972; Oku 1979; Weber 1994). It will be recognised that compounds derived from such a coupling reaction can be further functionalised. For example, a free hydroxyl group could be acylated or etherified using conventional synthetic methods. Representative examples of compounds prepared via these chemical synthetic pathways are depicted in FIG. 10.

Preparation of Caged Biotin—Gramicidin Complex (gAxx [B])

It will be recognised that a caged biotin could be used in place of a photoswitchable streptavidin ligand such as HABA (or a derivative) in the examples cited above, specifically those depicted in FIGS. 3, 4, and 5. Several caged biotin derivatives are known in the literature, such as those reported by Pirrung (1993, 1996). Such caged derivatives revert to biotin on irradiation with light and therefore cannot be switched between forms that bind streptavidin and forms that do not bind streptavidin.

An additional example of the use of such caged biotin compounds is depicted in FIG. 9.

i) manufacture (e.g. via evaporation) a gold coated substrate 94 on a surface (such as glass or silicon)

A photo-generatable derivative of biotin (so called caged biotin) was prepared by a modification of the method of Pirrung et al (*Bioconj. Chem.*, 1996, 7, 317). This compound (9 mg) was dissolved in dichloromethane (5 ml) and treated with dicyclohexylcarbodimide (DCC) (3 mg), N-hydroxy succinimide (NHS) (2 mg) and dimethylaminopyridine (0.2 mg). After stirring at room temperature for two hours a derivative of gramicidin bearing two aminocaproyl groups linked end-to-end and attached to the terminal hydroxyl of gramicidin (prepared by conventional peptide chemistry techniques) was added (30 mg, as a solution in methanol (1 ml) and triethylamine (0.1 ml)). The solution was stirred for 18 hours, evaporated to dryness and then passed through a Sephadex LH-20 column eluting with dichloromethanemethanol-water (800:50:4). The main fraction was then purified by HPLC on a 40 mm×200 mm Waters Prep Nova-Pak® HR silica column (6 µm, 6 Å) eluting with dichloromethane-methanol-water (800:40:4) operating at a flow rate of 25 ml/min. The fraction, eluting at 24.5 minutes, possessed a 1H-nmr spectrum and mass spectrum in full agreement with the proposed structure.

Investigation of Specific Photosensitive Chemistry in Ion Channel Sensing System Avidin/Streptavidin-biotin chemistry is one of the most widely used reactions in immunochemistry and is the strongest known noncovalent, biological interaction between a protein and a ligand, with $K_A=10^{15}M^{-1}$. The bond formation is very rapid and once formed, is unaffected by wide extremes of pH, temperature, organic solvents and other denaturing agents. Conditions which are usually sufficient for denaturing proteins fail to disassociate the avidin-biotin complex. A reporter molecule could be bound to streptavidin covalently, or biotinylated and attached to streptavidin via the straptavidin-biotin interaction. Selective activation and functionalisation of this complex is targeted in this group of experiments.

There are at least two applications that can be identified with the use of photosensitive compounds. The first one is using this chemistry for making the array and the other is for improving the signal by selectively filtering out the non-specific signals and other noise components. Both these applications can be used effectively either independently or together.

The following experiment was conducted with a form of biotin that is not active in the native state (i.e. will not bind to streptavidin) but can be activated by UV irradiation to bind streptavidin. This photoactivable form of biotin has been conjugated with gramicidin and used as an essential component of the bilayer membrane for targeting chemistries using streptavidin-biotin complex.

Materials and Methods

Preparation of Electrodes

The gold electrodes were built on commercially available glass microscope slides. The glass slides were cleaned for 2 hours in the glass cleaning solution "Extran 300", rinsed several times with copious volumes of deionised water and dried in a stream of nitrogen in clean rook conditions. The metal deposition was carried out using an Edwards evapor on unit. An adhesion layer of chromium (~20 nM) was deposited followed by a layer of gold (100 nM). One side of the glass slides was fully coated with metal. The metal treated glass slides were removed from the evaporator and quickly immersed in an ethanolic solution of monolayer components for an hour (AM300), rinsed profusely in ethanol and preserved in ethanol. These electrodes were stored at 4° C. for 24 hours before assembling the second layer of the membrane.

Preparation of Reagents and Biomolecules

Preparation of Solutions of Test Compound and Control Compounds

The photoactivable biotin in its native form has a molecular weight of 686 d and has a molecular weight of 2.809 kd in the form of gAxx[B]. This compound was dissolved in ethanol to prepare a 2 mM solution (5.5 mg in 1.958 ml) and further diluted to a 10 uM solution. An aliquot of the gAxx[B] solution was activated by irradiating the solution at 350 nM for a period of 20 minutes.

Figure 11:
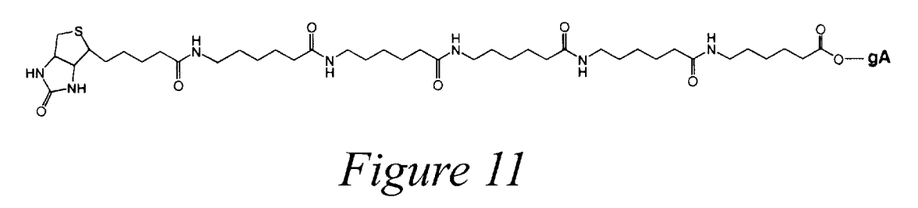
FIG. 11 show the structure of a caged biotin—gramicidin complex (gAxx[B])

Three types of second layer membrane solutions were prepared with 3 mM lipids DPEPC (1,2-di(3RS, 7R, 11R-phytanyl)-glycero-3-phosphocholine) and GDPE (1,2-di (3RS, 7R, 11R-phytanyl)-glycerol) in 7:3 ratio and three types of gA5xB. The first solution was prepared with gA5xB (see FIG. 11), the second with the inactive form of photoactivatable gAxx[B] and the third solution with the activated form of photoactivatable gAxx[B].

Streptavidin was diluted in PBS to a concentration of 0.1 mg/ml. The matched pair of biotinylated Thyroid Stimulating Hormone (TSH) Fabs (E20650M and E45650M) was combined in equal molar ratio to give a 50 ug/ml solution in PBS. TSH analyte was diluted in chilled PBS to prepare a 2.5 nM solution.

Assembling Biosensor Blocks

The monolayer AM300 was deposited on metallised glass electrodes as per established protocol. The electrodes were assembled into biosensor blocks. The second layer solution was added manually (15 µl per cell) and washed five times with PBS to assemble the bilayer membrane. The fully assembled blocks had the following second layers:

Block 1: Row A (cells 1–8) with a ratio of 40 k: 1 standard gA5xxB Row B (cells 9–16) with a ratio of 40 k 1 inactive for of gAxx[B]

Block 2: Same as above

Block 3: Row A (cells 1–8) with standard gA5xB as in blocks 1 and 2 Row B (cells 9–16) with the activated form of gAx[B].

A second group of 2 blocks were assembled with the inactive form of gAxx[B] and the cells were exposed to UV irradiation. The exposure time for pairs of cells was varied to study the effects of time length of exposure and select the most effective time period for future experiments. Exposure times down to one minute were found to be effective.

Observations

The inactive form of gAxx[B] did not show a binding response when treated with 42 nM streptavidin. This was reproducible and the positive control used in cells could be continued further to complete the TSH assay. The activated forms showed moderate response when exposed to streptavidin.

Cells 1–8 used the standard composition of second layer as a positive control for comparison and these responded to streptavidin. Cells 9–16 using the inactive form of gAxx[B] showed no response when exposed to streptavidin.

In the time course measurements the inactive gAxx[B] did not appear to facilitate a specific response as compared to the specific response elicited with standard gA5x[B].

Determination of the impedance responses showed that the activated form of gAxx[B] (test cells 9–16) showed a positive response to the addition of streptavidin. The inactive from of gAxx[B] did not facilitate any specific response. It may be concluded from these experiments that photoactivable select can be effectively activated by ultra violet irradiation to actively bind to streptavidin and allow gating of the biosensor.

It will be appreciated by persons skilled in the art that numerous variations and/or modifications may be made to the invention as shown in the specific embodiments without departing from a spirit or scope of the invention as broadly described. The present embodiments are, therefore, to be considered in all respects as illustrative and not restrictive.

REFERENCES

1. Pirrung et al, *J. Am. Chem. Soc.*, 1993, 115, 12050; Pirrung et al, *Bioconj. Chem.* 1996, 7, 137.
2. Berwick et al., *J. Org. Chem.*, 1972, 37, 2409.
3. Oku et al, *J. Org. Chem.*, 1979, 44, 3342.
4. Weber et al, *J. Am. Chem. Soc.*, 1994, 116, 2717.
5. Pillai, *Synthesis*, 1980, 1

What is claimed is:

1. A method of fabricating a biosensor in which there is at least one discrete zone linked to a ligand reactive with an analyte of interest and at least one discrete zone free of said ligand, the method comprising the following steps:
   (i) providing a conductive substrate;
   (ii) forming a membrane having an inner layer proximate a conductive substrate and an outer layer remote from the conductive substrate, the membrane comprising membrane spanning lipids and ion channels, the ion channels comprising first and second half membrane spanning monomers, the first half membrane spanning monomers being provided in the inner layer and the second half spanning monomers being provided in the outer layer, the membrane being attached to the conductive substrate in a manner such that a functioning reservoir exists between the membrane and the conductive substrate;
   (iii) linking a ligand reactive with an analyte of interest to the ion channel and linking a ligand reactive with an analyte of interest to the membrane spanning lipids via photocleavable linkers; and
   (iv) exposing at least one discrete zone of the membrane to a focused light source to cleave the photocleavable linkers therefrom thereby releasing the reactive ligands from the ion channel and membrane spanning lipids to form at least one discrete zone free of the reactive ligand and at least one zone linked to said reactive ligand.

2. A method as claimed in claim 1 in which the method further includes the following step:
   (v) binding control ligands to the ion channels and membrane spanning lipids after the reactive ligands have been removed in step (iv).

3. A method as claimed in claim 2 in which the membrane is rinsed between steps (iv) and (v).

4. A method of fabricating a biosensor in which there is at least one discrete zone comprising ligands reactive with an analyte of interest and at least one discrete zone comprising control ligands, the method comprising the following steps:
   (i) providing a conductive substrate;
   (ii) forming a membrane having an inner layer proximate a conductive substrate and an outer layer remote from the conductive substrate, the membrane comprising membrane spanning lipids and ion channels comprising first and second half membrane spanning monomers, the first half membrane spanning monomers being provided in the inner layer and the second half spanning monomers being provided in the outer layer, the membrane being attached to the conductive substrate in a manner such that a functioning reservoir exists between the membrane and the conductive substrate;
   (iii) providing on the ion channels and membrane spanning lipids a photoactivatable group which when illuminated will bind a receptor;
   (iv) illuminating at least one discrete zone of the membrane and linking a ligand reactive with an analyte of interest to the ion channel and membrane spanning lipids of the membrane via the photoactivated photoactivatable group to form zones linked to the reactive ligand;
   (v) removing unlinked reactive ligand; and
   (vi) linking a control ligand to the remainder of the ion channels and membrane spanning lipid components of the tethered membrane to form at least one zone linked to the control ligand.

5. A method as claimed in claim 4 in which the photoactivatable group is caged biotin.

6. An improved biosensor, the biosensor comprising a membrane and an electrode having a conductive substrate, the membrane having an inner layer proximate a conductive substrate and an outer layer remote from the conductive substrate, the membrane comprising membrane spanning lipids and ion channels comprising first and second half membrane spanning monomers, the first half membrane spanning monomers being provided in the inner layer and the second half spanning monomers being provided in the outer layer, the membrane being attached to the conductive substrate such that a functioning reservoir exists between the membrane and the conductive substrate, and ligands specific for an analyte attached the ion channels and membrane spanning lipids, the improvement comprising providing on at least one of the first and second half membrane spanning monomers a photocleavable/photoswitchable group which inhibits dimer formation.

7. A method of detecting the presence of an analyte in a sample, the method including the steps of:
   (i) providing the biosensor of claim 6 and adding a sample suspected to contain the analyte to the biosensor;
   (ii) determining the conductance or impedance of the membrane;
   (iii) exposing the biosensor to irradiation to which the photocleavable/switchable group is sensitive;
   (iv) determining the conductance or impedance of the membrane following irradiation; and
   (v) comparing the conductance or impedance determination in step (ii) with the determination in step (iv).

8. The method of claim 7, wherein steps (ii) to (v) are repeated.

9. An improved biosensor, the biosensor comprising a membrane and an electrode having a conductive substrate, the membrane having an inner layer proximate a conductive substrate and an outer layer remote from the conductive substrate, the membrane comprising membrane spanning lipids and ion channels comprising first and second half membrane spanning monomers, the first half membrane spanning monomers being provided in the inner layer and the second half spanning monomers being provided in the outer layer, the membrane being attached to the conductive substrate such that a functioning reservoir exists between the membrane and the conductive substrate, and ligands specific for an analyte attached the ion channels and membrane spanning lipids, wherein at least one of the ligands specific for an analyte attached the ion channels and membrane spanning lipids are attached by means of a photocleavable group or a photoswitchable group or a combination thereof.

10. A method of producing an improved biosensor, the method comprising the following steps:
   (i) providing a conductive substrate;
   (ii) forming a membrane having an inner layer proximate a conductive substrate and an outer layer remote from the conductive substrate, the membrane comprising membrane spanning lipids and ion channels comprising first and second half membrane spanning monomers, the first half membrane spanning monomers being provided in the inner layer and the second half spanning monomers being provided in the outer layer, the membrane being attached to the conductive substrate such that a functioning reservoir exists between the membrane and the conductive substrate;
   (iii) providing on the second half membrane spanning monomer a photoswitchable binder to streptavidin and providing biotin on the membrane spanning lipid;

(iv) adding streptavidin;

(v) triggering a light source and rinsing;

(vi) triggering the light source off and adding streptavidin; and (vii) adding ligands specific to an analyte to the ion channels and membrane spanning lipids.

11. The method of claim 10, wherein optionally steps (v) and (vi) are repeated prior to step (vii).

12. A method as claimed in claim 10 in which the photoswitchable binder to streptavidin is caged biotin or hydroxyazobenzene-benzoic acid.

13. An improved biosensor, the biosensor comprising a membrane and an electrode having a conductive substrate, the membrane having an inner layer proximate a conductive substrate and an outer layer remote from the conductive substrate, the membrane comprising membrane spanning lipids and ion channels comprising first and second half membrane spanning monomers, the first half membrane spanning monomers being provided in the inner layer and the second half spanning monomers being provided in the outer layer, the membrane being attached to the conductive substrate such that a functioning reservoir exists between the membrane and the conductive substrate, and ligands specific for an analyte attached to the ion channels and membrane spanning lipids, wherein at least one of the first and second half membrane spanning monomers, or the membrane spanning lipids, has thereon a photoswitchable group derived from a compound in accordance with Formula 1:

Formula 1 wherein $R_1$ represents 0 to about 3 groups where each is independently H or saturated or unsaturated, substituted or unsubstituted $C_{1-10}$ hydrocarbon; $R_2$ represents 0 to about 3 groups where each is independently hydrogen or saturated or unsaturated, substituted or unsubstituted $C_{1-10}$ hydrocarbon; Y represents H, saturated or unsaturated, substituted or unsubstituted $C_{1-10}$ hydrocarbon, $COR_6$, $CONR_7R_8$, $COOR_{14}$, $S(O)_nR_{15}$ where n is 0, 1 or 2, $R_6$, $R_7$, $R_8$, $R_{14}$ and $R_{15}$ are each independently represent H, saturated or unsaturated, substituted or unsubstituted $C_{1-10}$ hydrocarbon, or aryl; $R_9$ is —C(O)X where X represents H, saturated or unsaturated, substituted or unsubstituted $C_{1-10}$ hydrocarbon, or OH, or $OR_{10}$ in which $R_{10}$ is alkyl, or $NR_{11}R_{12}$ in which $R_{11}$ and $R_{12}$ are H, alkyl, or $R_{11}$, $R_{12}$ together with N form a ring, or aryl or $R_9$ together with $R_1$ form a substituted or unsubstituted 5–6 member cyclic or heterocyclic ring; Z represents O or $NR_{13}$ $R_{13}$ is H, saturated or unsaturated, substituted or unsubstituted $C_{1-10}$ hydrocarbon, or aryl, the compound including a functional group at Y or $R_9$ such that the compound can be linked to the at least one of the first and second half membrane spanning monomers.

* * * * *